United States Patent [19]

Butterfield

[11] Patent Number: 4,743,228
[45] Date of Patent: May 10, 1988

[54] FLUID FLOW MONITORING METHOD AND SYSTEM

[75] Inventor: Robert D. Butterfield, San Diego, Calif.

[73] Assignee: Ivac Corporation, San Diego, Calif.

[21] Appl. No.: 897,618

[22] Filed: Aug. 18, 1986

[51] Int. Cl.$^4$ ............................................. A61M 5/16
[52] U.S. Cl. ...................................... 604/50; 604/65; 604/245
[58] Field of Search ...................... 604/50, 65, 66, 67, 604/118, 244, 245

[56] References Cited

U.S. PATENT DOCUMENTS

| | | | |
|---|---|---|---|
| 4,217,993 | 8/1980 | Jess et al. | 604/65 X |
| 4,525,163 | 6/1985 | Slavik et al. | 604/65 |
| 4,534,756 | 8/1985 | Nelson | 604/65 X |
| 4,613,325 | 9/1986 | Abrams | 604/65 |

*Primary Examiner*—Edward M. Coven
*Attorney, Agent, or Firm*—Fulwider, Patton, Rieber, Lee & Utecht

[57] ABSTRACT

The invention is directed to a fluid flow monitoring method and system for parenteral fluid delivery systems for use in situations, such as with sedentary patients, when wide pressure variations are not expected. The resistance of the fluid delivery system is determined from the ratio of pressure differences at high and low fluid flow rates to differences in the high and low fluid flow rates. The resistance is used to develop a pressure limit from the sum of the pressure at low fluid flow rates and the product of the resistance and the high fluid flow rate. The pressure limit is compared with the pressure monitored and if the pressure monitored exceeds the calculated pressure limit, an alarm is actuated to warn medical personnel of an occlusion or other fluid flow fault. Additionally, if the noise level (pressure) excess predetermined limits during the periods of low and high fluid flow, the pressure monitoring is terminated.

21 Claims, 3 Drawing Sheets

FLUID FLOW MONITORING METHOD AND SYSTEM

BACKGROUND OF THE INVENTION

This invention generally relates to monitoring the flow of parenteral fluid through a fluid delivery system to a patient and particularly to a method and system for detecting infiltrations or other fluid flow faults in a fluid delivery system.

Fluid delivery systems for infusing parenteral fluid to a patient having positive pressure pumps have become fairly common. Typically, the infusion pump is a peristaltic type pump wherein a plurality of rollers, cams, or cam-actuated fingers sequentially constrict a flexible tube filled with parenteral fluid. Such fluid delivery systems also include, in addition to the pump, an inverted bottle of parenteral fluid, an intravenous (IV) set comprising a drip chamber, which is secured to the bottle of fluid, clear plastic tubing attached to the discharge end of the drip chamber, and a cannula which is mounted on the distal end of the tubing and which is adapted to be inserted into the patient's blood vessel to thereby deliver parenteral fluid. Roller clamps to manually control fluid flow rates, injection sites and pressure diaphragms and the like may also be provided with the IV set.

One common problem with many of the commercially available systems is the difficulty in evaluating the fluid flow within the delivery system in order to detect proper fluid communication between the fluid delivery system and the patient's blood vessels. Generally, if a fluid flow fault develops, the infusion pump will continue to deliver parenteral fluid notwithstanding such fluid flow fault. Thus, for example, if a needle delivering the fluid to the patient becomes dislodged from the vein so that the discharge tip of the needle lies in adjacent interstitial tissue, the fluid, which continues to be pumped, infiltrates the interstitial tissue and may cause serious injury. If the needle becomes dislodged from the patient, i.e., an open line, there may be no immediate injury, but the patient does not receive the fluid or drugs needed for treatment. Infiltrations and occlusions generally are characterized by an increase in fluid pressure within the fluid delivery system. Unfortunately, there are many other events which can also produce pressure increases within the fluid delivery system. As a result, many of the prior monitoring systems, which were based on the fluid pressure exceeding a predetermined amount, could not discriminate between infiltration or occlusions and these other pressure increasing events.

Methods and systems described in U.S. Pat. No. 4,534,756 (Nelson) and U.S. applications Ser. No. 872,086, filed on June 6, 1986, and Ser. No. 872,199, filed on June 6, 1986, assigned to the present assignee were substantial advances in the art of monitoring the administration of parenteral fluids to a patient and particularly for detecting fluid flow faults in such systems. However, in many instances, such as with sedentary patients, the sophisticated level of fluid flow monitoring described and claimed in the above patent and patent applications is not needed.

What has been needed and heretofore unavailable is a rudimentary control system for monitoring the fluid flow in a fluid delivery system which can readily discriminate fluid flow faults, such as infiltrations and the like, from normal fluid flow variations during periods when significant pressure variations are not expected. The present invention satisfies that need.

SUMMARY OF THE INVENTION

The present invention is directed to a simple, yet effective, fluid flow monitoring system and method which provides discrimination between normal fluid flow variations and fluid flow faults in those instances when significant pressure variations due to patient movement and other causes are not expected.

In accordance with this invention, the fluid pressure is monitored by a suitable transducer, and, when the pressure sensed exceeds an automatically determined pressure limit, a signal is generated to actuate an alarm indicating an occlusion or infiltration or other fluid flow fault so that medical personnel may take appropriate action. To minimize false alarms, it is preferred to require the sensed pressure to exceed the automatically determined pressure limit for a prescribed time period of flow before the alarm signal is generated.

The automatic pressure limit is determined in the following manner. First, the fluid flow rate through the delivery system is controlled (e.g., by the pump) at a first low rate ($F_{Low}$), preferably zero, and the pressure ($P_{Low}$) of fluid within the fluid delivery system is sensed. Then the fluid flow rate is controlled at a higher level ($F_{Hi}$), preferably the operating flow rate and the pressure ($P_{Hi}$) of fluid within the fluid delivery system is again sensed. The ratio of the differences in pressure to the differences in flow rate, i.e., $\Delta P/\Delta F$, is a measure of the resistance to fluid flow in the fluid delivery system. The term "resistance" is used herein in a generic sense which includes both resistance due to friction, obstructions and the like and impedance due to compliance and inertance of the system.

The automatic pressure limit ($P_{Lim}$) is a function of the product of the resistance (R) and high flow rate ($F_{Hi}$) and may be determined from the equation:

$$P_{Lim} = R \cdot F_{Hi} + K$$

where K is a constant. For an effective limit the constant K is the sum of $P_{Low}$, a factor relating to the pressure variations (noise) at the low fluid flow rate, and particularly the peak-to-peak value of pressure variations at zero flow rate, and an offset constant which is an added factor to minimize false alarms. For more consistent results, the values used in the calculations should be averaged or filtered values.

In a preferred embodiment, the pressure variations (noise) are monitored during both periods of low flow rate and high flow rate and, if any of the variations exceed predetermined limits, the automatic pressure limit program returns to the start which requires operator reactuation of the routine. Additionally, in the event that the resistance calculated exceeds a predetermined safe value, the automatic pressure limit is not determined and the program returns to the start which requires operator reactuation. In these instances a manually preset pressure limit is used as an alternate alarm system.

During the delivery of parenteral fluid to the patient, frequently, it is necessary to change the fluid flow rate. With the present system, a new pressure limit is automatically recalculated according to the new flow rate to provide a pressure limit which is more consistent with the new flow rate selected.

The pressure monitoring method and system of the invention is preferably included as an adjunct to the normal pressure sensing and control system of an infusion pump. As previously indicated, it is a monitoring mode which preferably must be selected by the operator. It presumes that the operator would have the professional competence to know when the pressure monitoring mode of the invention may be used, i.e., usually with sedentary, non-ambulatory patients.

To minimize unnecessary interruptions of the monitoring system of the invention due to noise, it is preferred to provide a time delay so that the noise must exceed the prescribed limit for a predetermined period before the system operation is interrupted. Generally, the delay period should not be greater than about ten seconds.

Thus, in accordance with the invention, a fluid flow monitoring method and system are provided which detect fluid flow faults under conditions when wide variations in fluid pressure is not expected. The system is preferably one that is selected by the operator and further one that does not become operational unless the short-term pressure variations (noise) and/or resistance within the fluid delivery system are below predetermined limits to ensure proper fluid communication between the fluid delivery system and the patient.

These and other advantages will become more apparent from the following detailed description of the invention when taken in conjunction with the accompanying exemplary drawings.

DETAILED DESCRIPTION OF THE INVENTION

Figure 1:
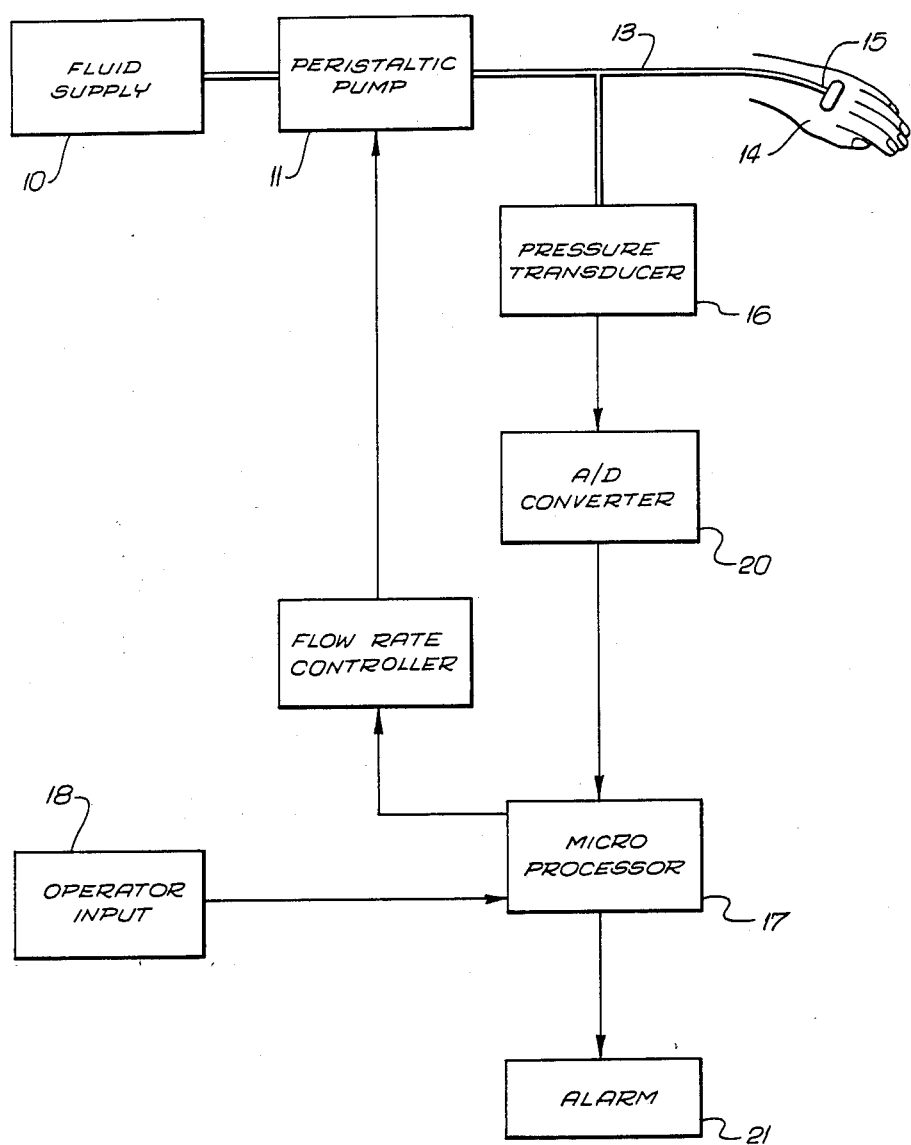
FIG. 1 is a schematic drawing of a fluid delivery monitoring system embodying features of the invention.

Reference is made to FIG. 1 which schematically illustrates a fluid delivery system embodying features of the invention. Generally, the system comprises a fluid supply 10, a pump 11, tubing 13 to transfer the parenteral fluid to a blood vessel in a patient's hand 14 through a cannula 15. A pressure transducer 16 monitors the pressure in the fluid delivery system and produces a signal representing the sensed pressure value. An analog to digital converter 20 converts the analog signal from the transducer 16 into digital signals which are transmitted to the microprocessor 17. The microprocessor 17 is provided with operator input unit 18 through which the operator sets the operational fluid flow rate and activates the automatic pressure monitoring system. The microprocessor 17 compares the sensed pressure in the tubing 13 with the calculated automatic pressure limit and generates an alarm signal to actuate alarm 21 in the event the pressure sensed exceeds the automatic pressure limit. A flow rate controller 25 provides a control signal to pump 11 to control the operation thereof to provide the desired flow rate, which is stored in microprocessor 17.

Figure 2:
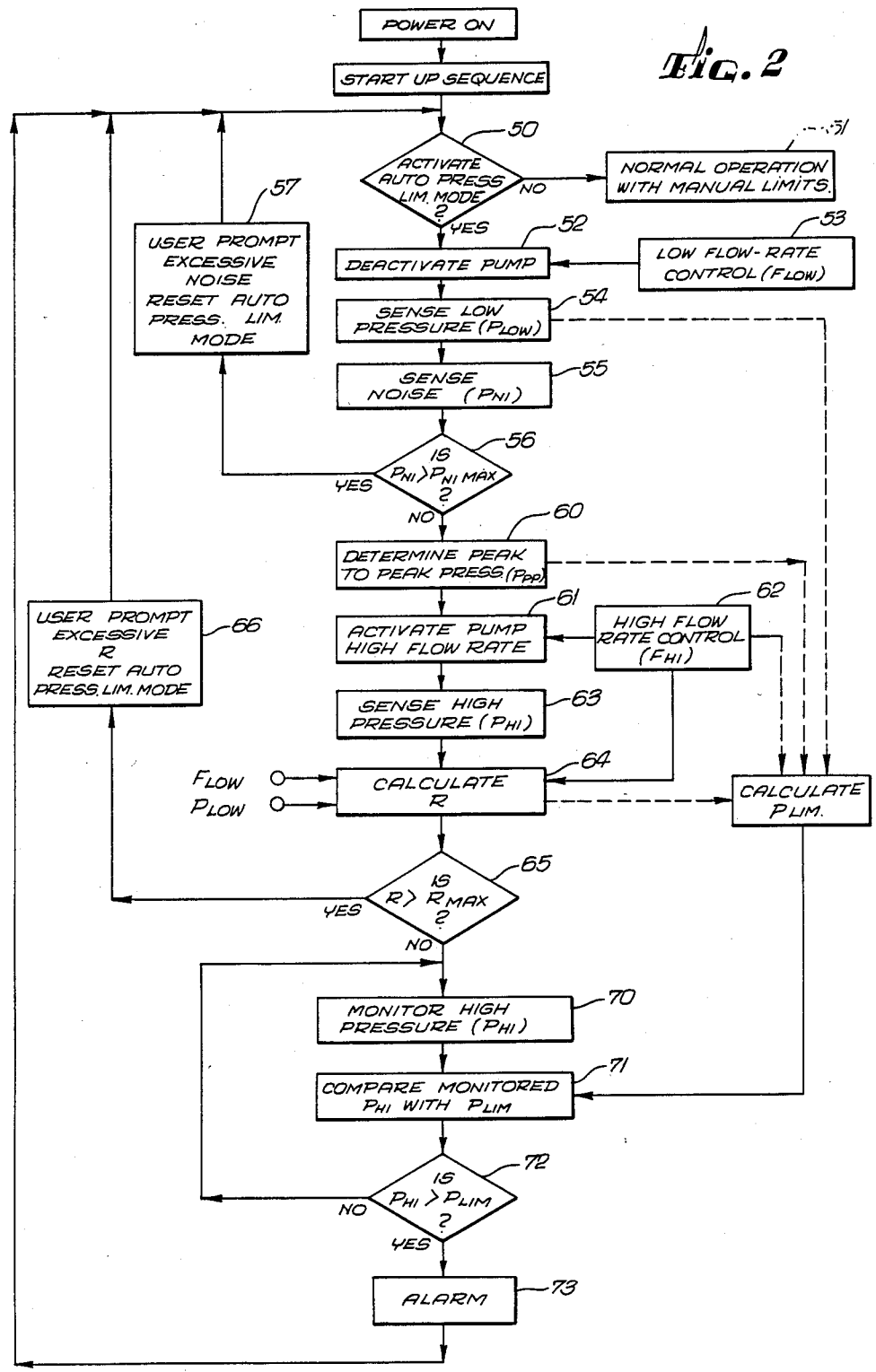
FIG. 2 is a flow diagram illustrating the operation of a monitoring system embodying features of the invention.
Figure 3:
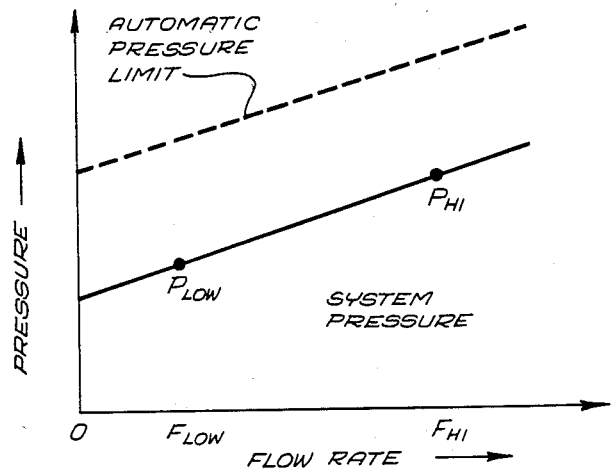
FIG. 3 provides graphical representations of pressure and flow rate relationships of the system pressure and the automatic pressure limit.

A flow chart is shown in FIG. 2 which reflects the operation of the invention. At the start 50 of the routine, the operator actuates the automatic pressure limit mode by pressing an appropriate switch or inputting the appropriate information to the microprocessor 17 at step 51. If the automatic pressure limit mode is not actuated, the program returns to normal operation with manualy set pressure limits. Upon actuation of the automatic pressure limit mode, the routine operation begins at step 52 by stopping the mechanism of pump 11 to provide a low (zero) fluid flow rate ($F_{Low}$) which is controlled by a signal from controller 25 at step 53. Shortly thereafter at step 54, the fluid pressure in tubing 13 is determined at essentially zero flow rate ($P_{Low}$) over a period of time. The short-term pressure variations or noise ($P_{N1}$) is determined at step 55 and if the determined values exceed a predetermined limit, as indicated by step 56, the routine returns to the start 50 and the operator is required to reactivate the automatic pressure limit routine. Preferably, the microprocessor has a user prompt at 57 to inform the operator that the pressure variations exceed the preset value (i.e., excessive noise). If the noise ($P_{N1}$) does not exceed the predetermined limit ($P_{N1max}$), the routine proceeds to step 60 where the peak-to-peak pressure ($P_{pp}$) over the zero flow rate period is determined. At step 61, the peristaltic pump 11 is actuated and controlled by a signal from controller 25 at 62 to provide the preselected operational fluid flow rate ($F_{Hi}$) and at step 63 the resulting fluid pressure ($P_{Hi}$) in the tubing 13 is monitored. The sensed pressure value ($P_{Hi}$) is used to compute the fluid flow resistance (R) at step 63 from the equation:

$$R = P_{Hi} - P_{Low}/F_{Hi} - F_{Low} \text{ or } \Delta P/\Delta F$$

The value for $P_{Hi}$ is received from step 63, the value for $P_{Low}$ from step 54 and the value for $F_{Hi}$ from step 62. $F_{Low}$ from step 53 is used only when a low flow rate other than zero is employed.

The calculated resistance (R) is compared at step 64 with a predetermined resistance limit ($R_{max}$) stored in microprocessor 17 and if the calculated resistance (R) exceeds the stored maximum resistance limit ($R_{max}$), a user prompt is actuated at step 65 to indicate excessive resistance to fluid flow in the fluid delivery system and the routine returns to step 50 wherein the operator may activate the automatic pressure limit mode.

If the resistance calculated at step 64 does not exceed the maximum resistance, an automatic pressure limit ($P_{Lim}$) is calculated at step 66 from the following equation:

$$P_{Lim} = R \cdot F_{Hi} + K$$

where K is the sum of system pressure at zero flow rate, a noise value relating to the peak-to-peak variations of pressure ($P_{pp}$) and a fixed offset constant.

Pressure monitoring of the flow of parenteral fluid through the delivery system is then initiated at step 70. The operating pressure sensed at the desired therapy level ($P_{Hi}$) is periodically compared at step 71 with the automatic pressure limit ($P_{Lim}$) from step 66 and, if at step 72 the pressure limit exceeds the automatic pressure limit, the alarm is actuated at step 73. If the sensed pressure does not exceed the automatic pressure limit at step 72, the routine returns to the pressure monitoring system at step 70. The monitoring continues until the sensed pressure exceeds the automatic pressure limit or the program is otherwise interrupted.

FIG. 2 graphically illustrates the relationship of pressure and flow rate of fluid within the delivery system for the automatic pressure limit ($P_{Lim}$) and the system pressure as set forth in the above equation. The difference between the $P_{Lim}$ and the system pressure at various flow rates is the constant K.

Figure 4:
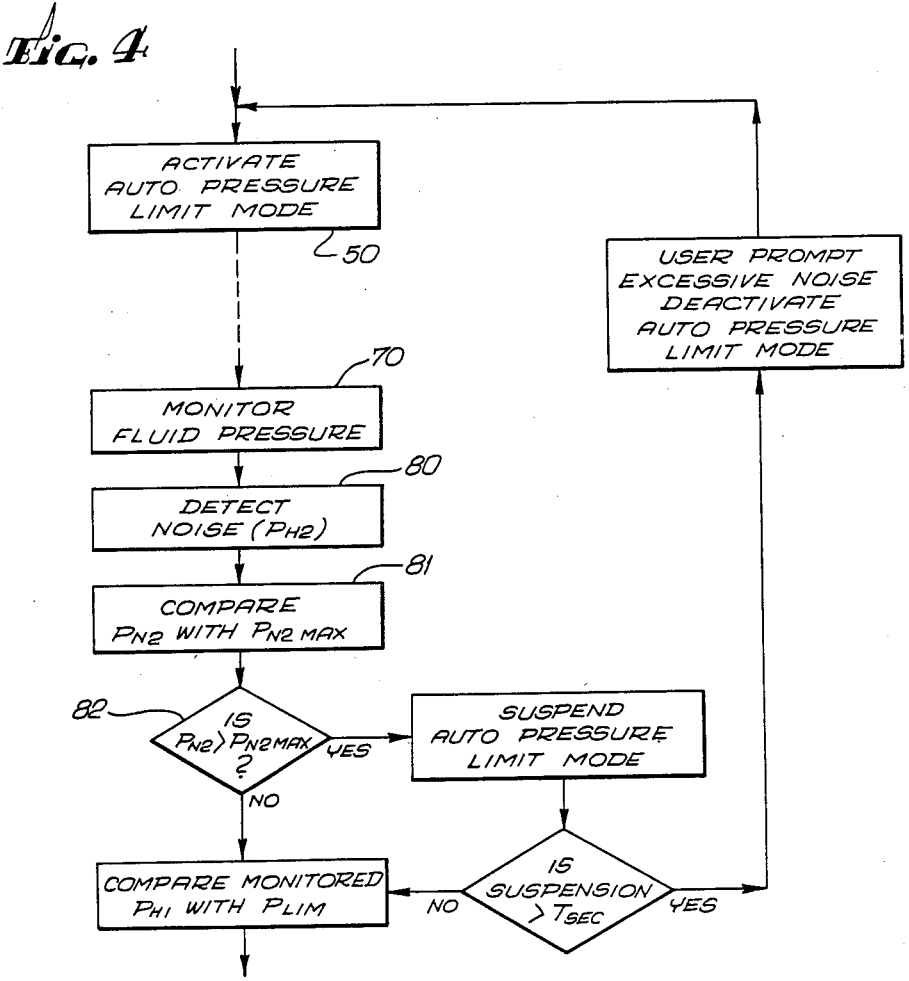
FIG. 4 is a flow diagram illustrating a modification of the embodiment illustrated in FIG. 2.

FIG. 4 illustrates a partial flow chart of a modification of the embodiment shown in FIG. 2. In this modification, the pressure variations ($P_{N2}$) at the high pressure level provided by high flow rates are determined at step 80 over a period of time during the pressure monitoring period. At step 81, sensed variations are compared with predetermined noise limits ($P_{N2max}$) from microprocessor 17, and if the sensed pressure variations ($P_{N2}$) at step 82 exceed the predetermined limit ($P_{N2max}$), the automatic pressure limit routine is suspended until the noise level returns to a value less than the maximum ($P_{NMax}$). If the term of the suspension is less than a prescribed time period, the routine returns to the comparing step 71. If the automatic pressure limit routine is temporarily suspended from more than the prescribed time, a user prompt is actuated at step 83 indicating excessive noise and the routine returns to the step 50 where the operator must reactivate the automatic pressure limit mode.

The pressure signals employed with the monitoring system should be filtered, preferably band pass filtered, e.g., 0.10 Hz to 10. Hz. Average or filtered values should be used in calculating resistance and pressure limits for more consistent results.

Other modifications and improvements can be made to the invention without departing from the scope thereof.

What is claimed is:

1. A system for monitoring the pressure of parenteral fluid in a fluid delivery system which includes a pump, tubing for transmitting pumped fluid to a cannula adapted to be inserted into a patient's blood vessel, the pressure monitoring system comprising:
    (a) means to control the rate of fluid flow through the delivery system to the patient at a predetermined low flow rate ($F_{Low}$) and at a predetermined high flow rate ($F_{Hi}$);
    (b) means to sense the fluid pressure within the fluid delivery system;
    (c) means to determine the difference in fluid pressure within the fluid delivery system during periods of the predetermined low flow rate and during period of the predetermined high flow rate;
    (d) means to determine the difference between the predetermined high flow rate and the predetermined low flow rate;
    (e) means to determine the resistance (R) of the fluid delivery system to fluid flow therethrough from the ratio of the fluid pressure difference to the fluid flow rate difference;
    (f) means to calculate a pressure limit ($P_{Lim}$) from the product of resistance (R) and the high flow rate ($F_{Hi}$);
    (g) means to compare the fluid pressure sensed within the fluid delivery system during a monitoring period with the calculated pressure limit ($P_{Lim}$); and
    (h) means to generate an alarm signal when the pressure sensed exceeds the calculated pressure limit.

2. The monitoring system of claim 1 including means to control the low fluid flow rate at essentially zero.

3. The monitoring system of claim 2 including means to determine pressure variations in the fluid delivery system when the fluid flow rate therethrough is at essentially zero.

4. The monitoring system of claim 1 wherein the means to calculate the pressure limit ($P_{Lim}$) from the product of the resistance and the high flow rate adds a constant K thereto.

5. The monitoring system of claim 4 wherein the constant K includes the fluid pressure ($P_{Low}$) during the predetermined low flow rate.

6. The monitoring system of claim 5 including means to detect the peak-to-peak values of pressure ($P_{pp}$) during the predetermined low flow rate.

7. The monitoring system of claim 6 wherein the constant K is the sum of $P_{Low}$ and the peak-to-peak values of pressure during periods of low flow rate and a fixed offset constant.

8. The monitoring system of claim 1 wherein the means to determine resistance (R) and to calculate the automatic pressure limit ($P_{Lim}$) is a microprocessor.

9. The monitoring system of claim 1 including means to determine fluid pressure variations.

10. The monitoring system of claim 9 including means to terminate the pressure monitoring system when the pressure variations exceed predetermined limits.

11. The monitoring system of claim 9 including means to terminate the operation of the monitoring system if the fluid pressure variations exceed predetermined limits for a predetermined time period or for a predetermined volume of fluid.

12. A method for monitoring the pressure of parenteral fluid in a fluid delivery system which includes a pump, tubing for transmitting pumped fluid to a cannula adapted to be inserted into a patient's blood vessel, the method of monitoring the pressure comprising:
    (a) controlling the rate of fluid through the delivery system to the patient at a predetermined low flow rate ($F_{Low}$) and at a predetermined high flow rate ($F_{Hi}$);
    (b) sensing the fluid pressure within the fluid delivery system;
    (c) determining the difference in fluid pressure within the fluid delivery system during the predetermined low flow rate and during the predetermined high flow rate;
    (d) determining the difference between predetermined the high flow rate and the predetermined low flow rate;
    (e) determining the resistance (R) of the fluid delivery system to fluid flow therethrough from the ratio of the pressure difference to the fluid flow rate difference;
    (f) calculating the pressure limit ($P_{Lim}$) from the product of the resistance (R) and the high flow rate ($F_{Hi}$);
    (g) comparing the fluid pressure ($P_{Hi}$) sensed within the fluid delivery system during a monitoring period with the calculated pressure limit ($P_{Lim}$); and
    (h) generating an alarm signal when the pressure sensed exceeds the calculated pressure limit.

13. The pressure monitoring method of claim 12 wherein the low fluid flow rate is at essentially zero flow.

14. The pressure monitoring method of claim 12 wherein the pressure limit ($P_{Lim}$) is calculated from the produce of the resistance K and the high flow rate and the sum thereof.

15. The pressure monitoring method of claim 14 wherein the constant K includes a factor representing the fluid pressure ($P_{Low}$) during low flow rate.

16. The pressure monitoring method of claim 14 including detecting the peak-to-peak value of pressure ($P_{pp}$) during periods of low flow rate.

17. The pressure monitoring method of claim 16 wherein the constant K is the sum of the flow rate ($P_{Low}$) and the peak-to-peak value of pressure ($P_{pp}$) during periods of flow rate.

18. The pressure monitoring method of claim 13 including determining pressure variations in the fluid delivery system.

19. The pressure monitoring method of claim 18 wherein the pressure variations detected are compared with a predetermined limit therefor.

20. The pressure monitoring method of claim 19 including terminating the pressure monitoring method when the pressure variations detected exceed the predetermined limits.

21. The pressure monitoring method of claim 19 including terminating the operation of the monitoring method if the fluid pressure variations exceed predetermined limits for a predetermined time period or for a predetermined volume of fluid flow.

* * * * *